(12) United States Patent
Niedzwiecki et al.

(10) Patent No.: US 10,716,767 B2
(45) Date of Patent: Jul. 21, 2020

(54) COMPOSITION FOR EYE HEALTH

(71) Applicants: Aleksandra Niedzwiecki, Aptos, CA (US); Matthias W Rath, Aptos, CA (US); Anna Goc, Sanjose, CA (US); Waldemar Sumera, Sanjose, CA (US)

(72) Inventors: Aleksandra Niedzwiecki, Aptos, CA (US); Matthias W Rath, Aptos, CA (US); Anna Goc, Sanjose, CA (US); Waldemar Sumera, Sanjose, CA (US)

(73) Assignee: Matthias W. Rath, Aptos, CA (US)

( * ) Notice: Subject to any disclaimer, the term of this patent is extended or adjusted under 35 U.S.C. 154(b) by 43 days.

(21) Appl. No.: 15/866,450

(22) Filed: Jan. 9, 2018

(65) Prior Publication Data
US 2019/0209489 A1    Jul. 11, 2019

(51) Int. Cl.
| | | |
|---|---|---|
| *A61K 31/07* | (2006.01) | |
| *A61K 31/375* | (2006.01) | |
| *A61K 31/355* | (2006.01) | |
| *A61K 31/198* | (2006.01) | |
| *A61K 31/385* | (2006.01) | |
| *A61K 31/047* | (2006.01) | |
| *A61P 27/02* | (2006.01) | |
| *A61K 36/28* | (2006.01) | |
| *A61K 36/15* | (2006.01) | |
| *A61K 36/87* | (2006.01) | |
| *A61K 36/45* | (2006.01) | |
| *A61K 33/30* | (2006.01) | |
| *A61K 31/01* | (2006.01) | |

(52) U.S. Cl.
CPC .............. *A61K 31/07* (2013.01); *A61K 31/01* (2013.01); *A61K 31/047* (2013.01); *A61K 31/198* (2013.01); *A61K 31/355* (2013.01); *A61K 31/375* (2013.01); *A61K 31/385* (2013.01); *A61K 33/30* (2013.01); *A61K 36/15* (2013.01); *A61K 36/28* (2013.01); *A61K 36/45* (2013.01); *A61K 36/87* (2013.01); *A61P 27/02* (2018.01)

(58) Field of Classification Search
None
See application file for complete search history.

(56) References Cited

U.S. PATENT DOCUMENTS

2003/0108624 A1* 6/2003 Kosbab .................. A61K 36/15
424/729

OTHER PUBLICATIONS

English translation of JP2003026589 retrieved from Espacenet on Mar. 28, 2018.*
Khazdair, M. R.; Boskabady, M. H.; Hosseini, M.; Rezaee, R.; Tsatsakis, A. M. The effects of *Crocus sativus* (saffron) and its constituents on nervous system: A review. Avicenna Journal of Phytomedicine, 2015, 376-391.*

* cited by examiner

*Primary Examiner* — Jessica Worsham
(74) *Attorney, Agent, or Firm* — Greeta Kadambi; Riddhi IP LLC

(57) ABSTRACT

The nutrient mixture made up of vitamin, carotenoid, micronutrient, essential trace element, and plant extract was much more effective in proactively protecting the corneal cells (human) and retinal pigment endothelial cells (rat) against damaging effects of $H_2O_2$ and glycosylated proteins (AGE-BSA) compared to its individual components. A mixture is made up of vitamin A, vitamin C, vitamin E, Lycopene, lutein, marigold flower extract, a saffron extract, pine bark extract, grape seed extract, bilberry extract, lipoic acid, L-Arginine and zinc.

6 Claims, 1 Drawing Sheet

COMPOSITION FOR EYE HEALTH

FIELD OF THE INVENTION

The subject matter disclosed in this application relates generally to the field of new composition or a nutrient mixture to be used for the improvement and management of eye health.

BACKGROUND OF THE INVENTION

Visual impairment due to preventable blindness is a life changing event for a child and the elderly in many developing countries. Giving a person their eye sight is one of the single most important gift that one human can provide another human. According to the National Health Institute and the National Geographic magazine conducted reported a survey in the September issue 2016, that 285 million people suffer from blindness worldwide. Out of those, 90% of the cases are in developing countries and 43% is preventable blindness. Preventable blindness is refractive errors and cataracts. Cataract mainly affects eye lens and opacity of the lens produces cataract. Vision is affected by many diseases including macular degeneration, diabetic retinopathy, corneal ulcerations, retinal detachment, glaucoma, etc., as well as various environmental factors that result in oxidative damage to eye cells and eye structural components. These include many metabolic diseases (i.e. diabetes), strong drug therapies such as cancer treatments, and other medications that produce oxidants which affect the retinal, lens and corneal among other cells involved in optimal vision process. Vision impairment management and maintenance is critical and should be a lifelong goal. Therefore, there is need to find a sustained, safe and economic solution for long term eye care.

SUMMARY OF THE INVENTION

The present invention discloses a mixture of various nutrients including micronutrients as a treatment to protect the eye components such as retinal pigment epithelial cells, lens and corneal cells from oxidative damage. In some embodiments of this invention is a new method of proactively protecting the eye tissue from damage due to preemptive intake of the said mixture is disclosed. In one embodiment, the deleterious effects of oxidants and glycosylated proteins on the parts of the eye of a mammal are disclosed. In another embodiment, a mixture being used as a pretreatment and post treatment for rectifying the damage caused by oxidants such as hydrogen peroxide and glycosylated proteins in the eye of a subject or a mammal are disclosed.

In one embodiment, A nutrient mixture, consisting of a vitamin, carotenoid, micronutrient, essential trace element, and plant extract, each component at a specific concentration, wherein the vitamin consists of a vitamin A, vitamin C and vitamin E, wherein the carotenoid consists of a Lycopene, and a lutein, wherein the plant extract consists of a marigold flower extract, saffron extract, pine bark extract, grape seed extract, bilberry extract, wherein the micronutrient consists of a lipoic acid and L-Arginine, wherein the essential trace element consists of a zinc is disclosed.

In one embodiment, a mixture consisting of vitamin A, vitamin C, vitamin E, Lycopene, lutein, marigold flower extract, saffron extract, pine bark extract, grape seed extract, bilberry extract, lipoic acid, L-Arginine and zinc to pretreat a retinal pigment epithelium and corneal cell of a mammal before the oxidative damage occurs to the retinal pigment epithelium and the corneal cell due to hydrogen peroxide or glycosylated proteins is disclosed.

A composition to protect corneal cell and retinal pigment epithelium of a subject from an oxidative damage, comprising: a mixture of a vitamin, micronutrient, carotenoid, essential trace element, and plant extract, wherein the vitamin consists of a vitamin A, vitamin C and vitamin E, wherein the carotenoid consists of a Lycopene and lutein, wherein the plant extract consists of a marigold flower extract, saffron extract, pine bark extract, grape seed extract, bilberry extract, wherein the micronutrient consists of a lipoic acid and L-Arginine, wherein the essential trace element consists of a zinc. Every component is mixed at a concentration in the mixture between 0.01-0.05 µg/ml in in-vitro conditions.

A mixture consisting of a vitamin A, a vitamin C, a vitamin E, a Lycopene, a lutein, a marigold flower extract, a saffron extract, a pine bark extract, a grape seed extract, a bilberry extract, a lipoic acid, a L-Arginine and a zinc to pretreat a retinal pigment epithelium and the corneal cell of a mammal after the oxidative damage occurs to the retinal pigment epithelium and corneal cell due to hydrogen peroxide or glycosylated proteins is disclosed. Each component in the mixture is added at concentration between 0.01-0.05 µg/ml in in-vitro conditions.

The physiological dose after calculation for mammal consumption is in the range of Vitamin A 20-20,000 IU, Vitamin C 1 mg-50, 000 g, Vitamin E 10 IU-40,000 IU, Arginine—10 mg-100 g, Alpha lipoic acid 10-2000 mg, Lutein 1-1000 mg, Lycopene 0.1-1000 mg, Marigold flower extract 1 mg-15,000 mg, Saffron extract—1 mg-10,000 mg, Pine bark extract—1 mg-10,000 mg, Grape seed extract-1 mg-10,000 mg, Bilberry extract—1-5000 mg and Zinc 0.1-1000 mg.

In one embodiment a method of using the nutrient combination in range of Vitamin A 20-20,000 IU, Vitamin C 1 mg-50, 000 g, Vitamin E 10 IU-40,000 IU, Arginine—10 mg-100 g, Alpha lipoic acid 10-2000 mg, Lutein 1-1000 mg, Lycopene 0.1-1000 mg, Marigold flower extract 1 mg-15, 000 mg, Saffron extract—1 mg-10,000 mg, Pine bark extract—1 mg-10,000 mg, Grape seed extract-1 mg-10,000 mg, Bilberry extract—1-5000 mg and Zinc 0.1-1000 mg for treating oxidative stress, eye disease and cancer is disclosed.

More specifically the nutrient mixture is used for treating and protecting corneal cells and retinal pigment epithelium using the range of Vitamin A 20-20,000 IU, Vitamin C 1 mg-50, 000 g, Vitamin E 10 IU-40,000 IU, Arginine—10 mg-100 g, Alpha lipoic acid 10-2000 mg, Lutein 1-1000 mg, Lycopene 0.1-1000 mg, Marigold flower extract 1 mg-15, 000 mg, Saffron extract—1 mg-10,000 mg, Pine bark extract—1 mg-10,000 mg, Grape seed extract-1 mg-10,000 mg, Bilberry extract—1-5000 mg and Zinc 0.1-1000 mg. The nutrient mixture may be packaged in different drug formulations and administered to a mammal for proactive treatment and after the disease has manifested as a treatment method.

The nutrients in the nutrient mixture may be substituted, added or subtracted from original combination and new ingredients may be added to have beneficial effect. Finally, the present invention is described further in the detailed description to further illustrate various aspects of the present invention.

BRIEF DESCRIPTION OF THE FIGURES

Example embodiments are illustrated by way of example and not limitation in the figures of the accompanying drawings, in which like references indicate similar elements and in which.

Figure 1:
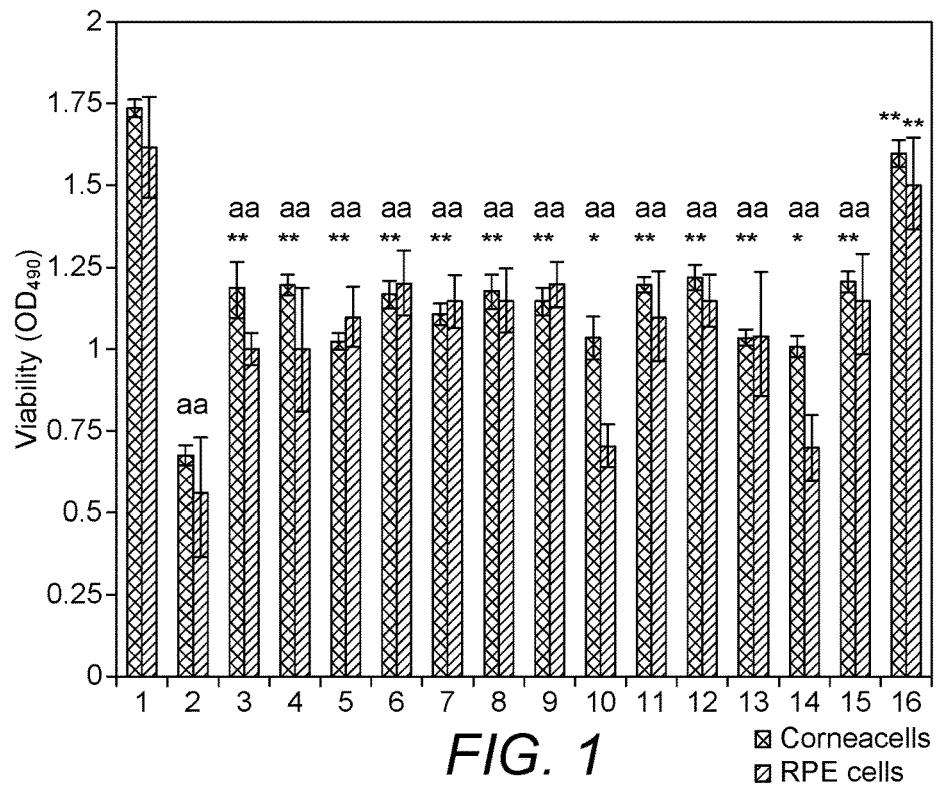
FIG. 1. In vitro viability assay of rat eye RPE and human corneal cells pre-treated with different micronutrients and plant extracts (0.01-0.05 µg/ml) for 24 h at 37° C. and exposed to 2 mM of hydrogen peroxide for 30 min.

Others features of the present embodiments will be apparent from the accompanying drawings and from the detailed description that follows.

DETAILED DESCRIPTION

The following embodiments are described for illustrative purposes only with reference to the Figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Oxidative damage due to various chronic disease as well as metabolic disease takes a toll on internal organs and their parts. The onslaught of oxidants is continuous and very difficult to reverse. Hydrogen peroxide and glycosylated proteins such as glycosylated hemoglobin and others have shown to damage the retinal epithelial cells, cornea and eye lens in diabetes and not just limited to diabetes. There are plethora of articles that corroborates that oxidative stress is very harmful for eye health and there needs to be a sustained treatment for reducing the damage and keeping the eye cells healthy for the long run. Various therapies involving vitamin combinations or mineral or micronutrients have been tried before after the diagnosis of diabetes mellitus to slow down the oxidant damage in the eyes. However, no study suggests pretreatment of specific mixture as claimed to be effective in reducing and preserving the health of the retinal pigment epithelium and corneal cells in mammals.

Primary effects of the combination to achieving comprehensive antioxidant protection by the nutrient mixture not just only for the eye tissues and membranes but for any tissue or organ facing oxidant threat due to a disease. The disease may be diabetes, cancer, chemotherapy, UV ray induced damage or similar pathway inflicted diseases. We discuss the benefits of each ingredient to decrease negative effects of oxidative damage for a specific function but the combination has never been used as a nutrient mixture to enable pretreatment or administration of these components before the disease even occurs or after a mild form of the disease or beginning of the symptoms of the said diseases:

Vitamin A—It is known as important for vision, especially night vision.

Vitamin C— the most potent antioxidant, protects watery part of cells that can result in reducing ocular pressure in glaucoma patients.

Vitamin E—lipid soluble antioxidant.

Lipoic acid—antioxidant component which is integral to antioxidant recycling process. A lack of lipoic acid reduces the ability of other antioxidants to protect cells.

Carotenoids—include eye protective pigments such as lutein, lycopene or beta-carotene. Arginine—a source of NO improving blood flow to the eyes.

Zinc—a trace element essential for bringing vitamin A from the liver to the retina to produce melanin, a protective pigment in the eyes. Zinc is highly concentrated in the eye, mostly in the retina and choroid (the vascular tissue layer under the retina). Important for optimum night vision. It is also essential for the function of superoxide dismutase (Cu—Zn), an antioxidant enzyme protecting against damage from superoxide radicals.

Marigold extract is a natural source of lutein, zeaxanthin and other potent antioxidants beneficial in eye health. Saffron extract—this spice contains the antioxidant carotenoids crocin and crocetin among other ingredients, with strong antioxidative, cellular and neuro-protective properties.

Pine bark extract has high contents of potent antioxidants known as oligomeric proanthocyanidins, or OPCs. These compounds have anti-inflammatory properties and protect endothelium against oxidative damage.

Grape seed extract—its active ingredient is oligomeric proanthocyanidins (OPCs). OPCs display antioxidants and antihistamine properties. Grape seeds also contain vitamin E, flavonoids and linolenic acid important for eye function.

Bilberry extract—a potent source of antocyanins with antioxidant and metal chelating properties. It also contains other antioxidant components such as vitamin C, quercetin and catechins. The extract displays strong antioxidant properties, also effective in lowering blood sugar that damages blood vessels and eye structures.

Comprehensive expected physiological effects of the combination: Table 1:

| Function | Benefit from: |
| --- | --- |
| Eye ciliary muscles - their optimum contraction and relaxation control focusing of the lens | Arginine, vitamin E and C |
| Epithelial cells of the retina and macula that support vision | Vitamin A, lutein, beta-carotene, carotenoids, grape seed extract, pine bark extract |
| Functional and protective pigments of the macula | Vitamin A, lutein and other carotenoids, Zinc, marigold flower extract, grape seed extract |
| Myelin sheets of the optic nerve that transport impulses to the brain to create images | Vitamin C, E, lipoic acid, saffron extract |
| Blood vessels in the eyes that provide oxygen and nutrients to eyes. Support for optimum blood flow | Arginine -the source of NO- for relaxing blood vessel walls, Vitamin C (elasticity and integrity of blood vessel walls), grape seed extract and vitamin E (optimizing blood viscosity) |
| Metabolic effects | Vitamin C, Zinc, bilberry extract, lipoic acid (support in optimizing sugar levels), vitamin |

| Function | Benefit from: |
|---|---|
| | C (optimizing cholesterol levels), all compounds (protection against oxidative stress and inflammation) |

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Materials and Methods

The following compounds of the nutrient mixture, with the purity between 90%-98% according to the manufacturer, were obtained from Sigma (St. Louis, Mo.): vitamin c, NAC, lycopene, lutein, and lipoic acid. The compounds: L-arginine, grape seed extract, and pycnogenol/pine bark extract, with the purity between 90%-98% according to the manufacturer, were purchased from Powder City (York, Pa.). Vitamin E, zinc, bilberry extract, marigold (calendula) extract, and saffron extract with the purity between 97%-99% according to the manufacturer, was from Monterey Bay Spice (Watsonville, Calif.). All cell lines were from ATCC (Manassas, Va.).

Methods:

The following assays were performed according to published report by Chatterjee et al. J. Cell. Med. Nat. Health 2016; June 15:1-10.

In Vitro Cells Protection Assay Against Oxidative Stress:

Cells (i.e., primary human corneal cells and rat RPE-J cells, respectively) were grown to monolayer in 96-well plate in DMEM 10% FBS medium. Next, cells were pre-treated with individual ingredients and mix of them for 24 hours, respectively. Afterwards, media was removed, cells were exposed to 2 mM $H_2O_2$ for 30 minutes, then washed once with 1×PBS, and incubated in DMEM 1% BSA for 24 hours. Next, viability assay was performed using CellTiter 96® AQueous One Solution Cell Proliferation Assay from Promega (Sunnyvale, Calif.) The CellTiter 96, which is a colorimetric method for determining the number of viable cells in proliferation or cytotoxicity assay. Optical density was measured at 490 nm.

In vitro cells protection assay against glucose damage induced by AGE-BSA: Cells (i.e., primary human corneal cells and rat RPE-J cells, respectively) were grown to monolayer in 96-well plate in DMEM 10% FBS medium. Cells were co-treated with 550-750 μg/ml advanced glycated endproduct-bovine serum albumin (AGE-BSA) together with ingredients and mix of them for 24 hours, respectively. Glycoaldehyde-AGE modified BSA was used in this assay as an agent mimicking damage caused by glucose that was purchased from Biovision (Milpitas, Calif.). Afterwards, media was removed, cells were washed once with 1×PBS and viability assay was performed using CellTiter 96® AQueous One Solution Cell Proliferation Assay from Promega (Sunnyvale, Calif.). Optical density was measured at 490 nm Statistical analysis. Means and standard deviations were determined for all experiments and Student's t test analysis was used to determine significant differences. Statistical analysis was performed by two-sample paired t-test using GraphPad statistical software.

FIG. 1 shows in-vitro viability assay of rat eye RPE and human corneal cells pre-treated with different micronutrients and plant extracts (0.01-0.05 m/ml) for 24 h at 37° C. and exposed to 2 mM of hydrogen peroxide for 30 min. Values shown are mean±standard deviation (n=4); Value significantly different from corresponding control at *p<0.05-0.01, **p<0.001 compared to positive control ($H_2O_2$); $^a$ p<0.01-0.001 compared to negative control. FIG. 1 columns are represented as follows in Table 2. The use of the nutrient mixture for the protection of a corneal cell or retina pigment epithelial cell may done using the composition of a vitamin, carotenoid, micronutrient, essential trace element, and plant extract, each component at a specific concentration, wherein the vitamin consists of a vitamin A, vitamin C and vitamin E, wherein the carotenoid consists of a Lycopene, and a lutein, wherein the plant extract consists of a marigold flower extract, saffron extract, pine bark extract, grape seed extract, bilberry extract, wherein the micronutrient consists of a lipoic acid and L-Arginine, wherein the essential trace element consists of a zinc. Each component of the nutrient mixture is in the range of 0.01-0.05 m/ml in vitro conditions.

TABLE 2

1. Negative Control
2. Positive control (hydrogen peroxide)
3. Vitamin C
4. Vitamin E
5. Vitamin A
6. L-arginine
7. Grape seed extract
8. Lipoic acid
9. Marigold flower (*Calendula*) extract
10. Lutein
11. Lycopene
12. Bilberry extract
13. Pycnogenol/Pine bark extract
14. Zinc
15. Saffron extract
16. Nutrient Mixture The viability of both types of eye-sourced cells pretreated with the mixture of 12 tested compounds before their exposure to $H_2O_2$ was dramatically higher compared to the control cells which were exposed to hydrogen peroxide only. Column 2 to 16 when compared with each other shows very different out comes for individual ingredients but the mixture shows dramatic improvement in cell viability. Since all the ingredients have no left over side effects and all components are chosen carefully to have additive effect the viability is significantly affected and shows beneficial effect of the mixture. Various literatures have shown that antioxidant vitamin and trace element intakes have been shown to be particularly important in the prevention of cancer, cardiovascular diseases, age related ocular diseases and in aging. In animal models, targeted interventions have been associated with reduction of tissue destruction is brain and myocardium ischemia-reperfusion models. In the critically ill antioxidant supplements have resulted in reduction of organ failure and of infectious complications. There is no evidence of the said mixture being used for preventing oxidative damage caused by $H_2O_2$ for eye cells.

The mixture was significantly more effective in protecting these cells than its individual compounds (compare columns 3 through 16). There were no significant differences in protective effects of tested compounds between human corneal and rat RPE cells. Pre-treatment of cells with the Mixture made cells almost fully resistant to damaging effects of $H_2O_2$ (compare columns 1 and 16).

Figure 2:
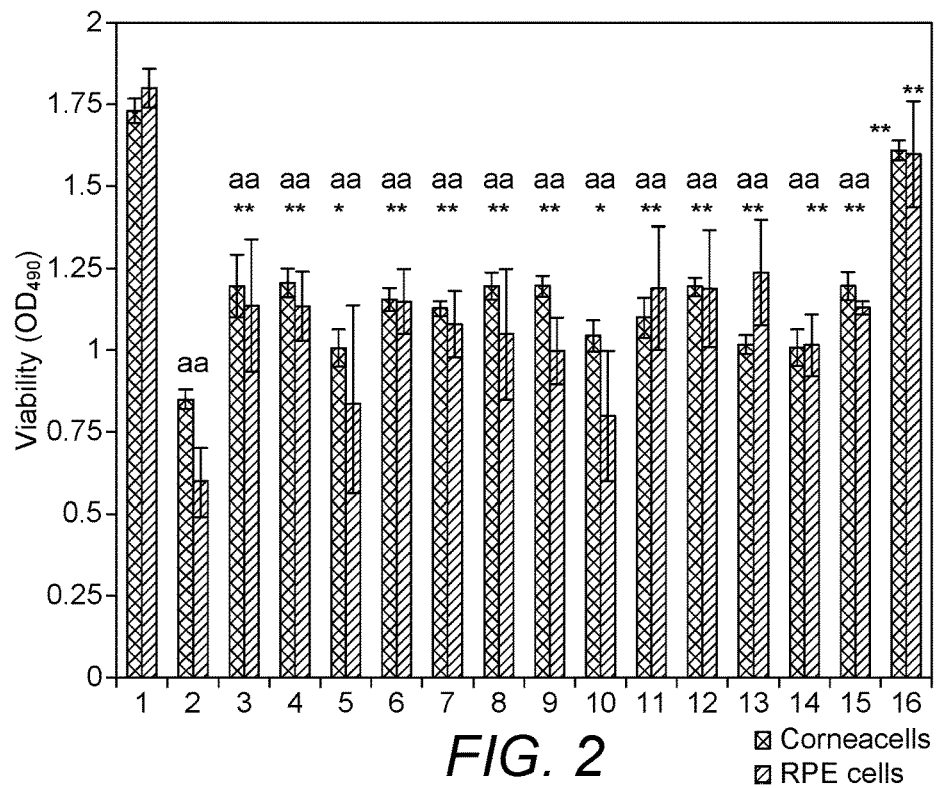
FIG. 2. In vitro viability assay of rat eye RPE and human corneal cells treated with different micronutrients and plant extracts (0.01-0.05 µg/ml) together with 550-750 µg/ml of glycoaldehyde-AGE modified BSA for 24 h at 37° C.

FIG. 2. In vitro viability assay of rat eye RPE and human corneal cells treated with different micronutrients and plant extracts (0.01-0.05 μg/ml) together with 550-750 μg/ml of glycoaldehyde-AGE modified BSA for 24 h at 37° C. Values shown are mean±standard deviation (n=4); Value significantly different from corresponding control at * $p<0.05$, ***$p<0.001$; a $p<0.01$ compared to positive control (AGE-BSA); *$p<0.0$-0.01, ** $p<0.001$ compared to positive control (AGE-BSA); $^a$ $p<0.01$-0.001 compared to negative control. FIG. 2 bars are depicted as follows in Table 3:

1. Negative Control
2. Positive control (AGE-BSA)
3. Vitamin C
4. Vitamin E
5. Vitamin A
6. L-arginine
7. Grape seed extract
8. Lipoic acid
9. Marigold flower (*Calendula*) extract
10. Lutein
11. Lycopene
12. Bilberry extract
13. Pycnogenol/Pine bark extract
14. Zinc
15. Saffron extract
16. Nutrient Mixture Both types of eye-sourced cells exposed to the mixture of 12 tested compounds in the nutrient mixture in the presence of AGE-BSA which mimics the damage caused by glucose showed a high level of survival compared to the cells exposed to AGE-BSA only. (compare columns 2 and 16). Glycosylation of protein once occurred is very difficult to reverse and has a cascading bad effect on several enzyme activities in combating oxidative stress as well as impairs cellular metabolism overall. Hence pretreatment and sustained treatment is beneficial to mitigate oxidative stress.

The mixture was significantly more effective in protecting these cells than its individual compounds (compare columns 3 through 16). The experiment shows that RPE cells are more sensitive to glucose-induced damage than corneal cells (the bars in Line 2). This trend seems to persist also in the presence of different ingredients, but it is not statistically significant (compare columns 3 through 16). In the presence of the mixture both types of cells are almost fully resistant to damaging effects of glucose (compare columns 1 and 16).

The mixture of all tested nutrient mixtures was much more effective in protecting corneal cells (human) and retinal pigment endothelial cells (rat) against damaging effects of $H_2O_2$ and glycosylated proteins (AGE-BSA) compared to its individual components. Administering the nutrient mixture of a vitamin A, a vitamin C, a vitamin E, a Lycopene, a lutein, a marigold flower extract, a saffron extract, a pine bark extract, a grape seed extract, a bilberry extract, a lipoic acid, a L-Arginine and a zinc in solid or liquid form to a mammal having a disease that produces an oxidant in their body. The individual compounds in the nutrient mixture are between 0.01-0.05 μg/ml. The physiological dose may be calculated for consumption by mammals based on absorption, age, weight and severity etc. of the subject and disease. The physiological dose after calculation for mammal consumption is in the range of Vitamin A 20-20,000 IU, Vitamin C 1 mg-50, 000 g, Vitamin E 10 IU-40,000 IU, Arginine—10 mg-100 g, Alpha lipoic acid 10-2000 mg, Lutein 1-1000 mg Lycopene 0.1-1000 mg, Marigold flower extract 1 mg-15,000 mg, Saffron extract—1 mg-10,000 mg, Pine bark extract—1 mg-10,000 mg, Grape seed extract—1 mg-10,000 mg, Bilberry extract—1-5000 mg and Zinc 0.1-1000 mg. These concentrations may be applied to all drug formulations discussed below. In one embodiment, all of the components, or substitutions, subtractions and additions for each component of the nutrient mixture may be performed with artificial, natural or synthetic chemicals to serve the beneficial purpose of combating oxidative damage in diseases.

Drug formulations suitable for these administration routes can be produced by adding one or more pharmacologically acceptable carriers to the agent and then treating the mixture through a routine process known to those skilled in the art. The mode of administration includes, but not limited to, are non-invasive peroral, topical (example transdermal), enteral, transmucosal, targeted delivery, sustained release delivery, delayed release, pulsed release and parenteral methods. Peroral administration may be administered both in liquid and dry state.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions may also be administered as a bolus, electuary, or paste.

When an oral solid drug product is prepared, nutrient mixture is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder, or capsules. Additives may be those generally employed in the art. Examples of the excipient include lactate, sucrose, sodium chloride, glucose, starch, calcium carbonate, kaolin, microcrystalline cellulose, and silicic acid; examples of the binder include water, ethanol, propanol, simple syrup, glucose solution, starch solution, liquefied gelatin, carboxymethylcellulose, hydroxypropylcellulose, hydroxypropyl starch, methyl cellulose, ethyl cellulose, shellac, calcium phosphate, and polyvinyl pyrrolidone; examples of the disintegrant include dried starch, sodium arginate, powdered agar, sodium hydrogencarbonate, calcium carbonate, sodium lauryl sulfate, monoglyceryl stearate, and lactose; examples of the lubricant include purified talc, stearic acid salts, borax, and polyethylene glycol; and examples of the sweetening agent include sucrose, orange peel, citric acid, and tartaric acid.

When a liquid drug product for oral administration is prepared, nutrient mixture is mixed with an additive such as a sweetening agent, a buffer, a stabilizer, or a flavoring agent, and the resultant mixture is processed through a routine method, to thereby produce an orally administered liquid drug product such as an internal solution medicine, syrup, or elixir. Examples of the sweetening agent include vanillin; examples of the buffer include sodium citrate; and examples of the stabilizer include tragacanth, acacia, and gelatin.

For purposes of transdermal (e.g., topical) administration, dilute sterile, aqueous or partially aqueous solutions (usually in about 0.1% to 5% concentration), otherwise similar to the above parenteral solutions, may be prepared.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

A targeted release portion can be added to the extended release system by means of either applying an immediate release layer on top of the extended release core; using coating or compression processes or in a multiple unit system such as a capsule containing extended and immediate release beads.

When used with respect to a pharmaceutical composition or other material, the term "sustained release" is art-recognized. For example, a therapeutic composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

Current efforts in the area of drug delivery include the development of targeted delivery in which the drug is only active in the target area of the body (for example, in cancerous tissues) and sustained release formulations in which the drug is released over a period of time in a controlled manner from a formulation. Types of sustained release formulations include liposomes, drug loaded biodegradable microspheres and drug polymer conjugates.

Delayed release dosage formulations are created by coating a solid dosage form with a film of a polymer which is insoluble in the acid environment of the stomach, but soluble in the neutral environment of the small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Alternatively, a delayed release tablet may be formulated by dispersing tire drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

A pulsed release-dosage is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

The phrases "parenteral administration" and "administered parenterally" as used herein refer to modes of administration other than enteral and topical administration, such as injections, and include without limitation intravenous, intramuscular, intrapleural, intravascular, intrapericardial, intra-arterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

Certain pharmaceutical compositions disclosed herein suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic within the blood of the intended recipient or suspending or thickening agents.

When an injection product is prepared, nutrient mixture is mixed with an additive such as a pH regulator, a buffer, a stabilizer, an isotonicity agent, or a local anesthetic, and the resultant mixture is processed through a routine method, to thereby produce an injection for subcutaneous injection, intramuscular injection, or intravenous injection. Examples of the pH regulator or buffer include sodium citrate, sodium acetate, and sodium phosphate; examples of the stabilizer include sodium pyrosulfite, EDTA, thioglycollic acid, and thiolactic acid; examples of the local anesthetic include procaine hydrochloride and lidocaine hydrochloride; and examples of the isotonicity agent include sodium chloride and glucose.

The phrase "pharmaceutically acceptable" is art-recognized. In certain embodiments, the term includes compositions, polymers and other materials and/or dosage forms which are within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical compositions described herein are formulated in a manner such that said compositions will be delivered to a mammal in a therapeutically effective amount, as part of a prophylactic, preventive or therapeutic treatment.

In certain embodiments, the dosage of the nutrient mixture compositions, which may be referred as therapeutic composition provided herein may be determined by reference to the plasma concentrations of the therapeutic composition or other encapsulated materials.

The therapeutic compositions provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

Expressed in terms of concentration, an active ingredient can be present in the therapeutic compositions of the present invention for localized use about the cutis, intranasally, pharyngolaryngeally, bronchially, intravaginally, rectally, or ocularly.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The most common routes of administration also include the preferred transmucosal (nasal, buccal/sublingual, vaginal, ocular and rectal) and inhalation routes.

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants. The therapeutic acceptable dosage of the nutrient mixture may be combined with other drugs and may be treated as a combination drug.

What is claimed is:

1. A nutrient mixture, consisting of:
a vitamin, carotenoid, micronutrient, essential trace element, and plant extract, each component at a specific concentration, wherein the vitamin consists of a Vitamin A, Vitamin C and Vitamin E, wherein the carotenoid consists of a Lycopene, and a Lutein, wherein the plant extract consists of a Marigold flower extract, Saffron extract, Pine bark extract, Grape seed extract, and Bilberry extract, wherein the micronutrient consists of an Alpha lipoic acid and a L-Arginine, and wherein the essential trace element consists of a Zinc, wherein the nutrient mixture pretreats a retinal pigment epithelium and corneal cell of a mammal before an oxidative damage occurs to the retinal pigment epithelium and the corneal cell.

2. The nutrient of claim 1, wherein the specific concentration of Vitamin A is 20 IU-20,000 IU, Vitamin C is 1 mg-50,000 g, Vitamin E is 10 IU-40,000 IU, L-Arginine is 10 mg-100 g, Alpha lipoic acid is 10 mg-2000 mg, Lutein is 1 mg-1000 mg, Lycopene is 0.1 mg-1000 mg, Marigold flower extract is 1 mg-15,000 mg, Saffron extract is 1 g-10,000 mg, Pine bark extract is 1 g-10,000 mg, Grape seed extract is 1 g-10,000 mg, Bilberry extract is 1 mg-5000 mg and Zinc is 0.1 g-1000 mg.

3. A nutrient mixture consisting of a Vitamin A, a Vitamin C, a Vitamin E, a Lycopene, a Lutein, a Marigold flower extract, a Saffron extract, a Pine bark extract, a Grape seed extract, a Bilberry extract, an Alpha lipoic acid, a L-Arginine and a Zinc to pretreat a retinal pigment epithelium and corneal cell of a mammal before an oxidative damage occurs to the retinal pigment epithelium and the corneal cell due to hydrogen peroxide produced in the body due to oxidative stress or due to exposure to glycosylated proteins or an advanced glycated end product-bovine serum albumin.

4. The nutrient mixture of claim 3, wherein a specific concentration of Vitamin A is 20 IU-20,000 IU, Vitamin C is 1 mg-50,000 g, Vitamin E is 10 IU-40,000 IU, L-Arginine is 10 mg-100 g, Alpha lipoic acid is 10 mg-2000 mg, Lutein is 1 mg-1000 mg, Lycopene is 0.1 mg-1000 mg, Marigold flower extract is 1 g-15,000 mg, Saffron extract is 1 mg-10,000 mg, Pine bark extract is 1 mg-10,000 mg, Grape seed extract is 1 mg-10,000 mg, Bilberry extract is 1 mg-5000 mg and Zinc is 0.1 mg-1000 mg.

5. A method of using a nutrient mixture, consisting of: a Vitamin A
, a Vitamin C, a Vitamin E, a Lycopene, a Lutein, a Marigold flower extract, a Saffron extract, a Pine bark extract, a Grape seed extract, a Bilberry extract, an Alpha lipoic acid, a L-Arginine and a Zinc comprising administering the nutrient mixture in a solid or liquid form to a mammal having a disease that produces an oxidative damage in the mammal.

6. The method-of claim 5, wherein a specific concentration of the Vitamin A is 20 IU-20,000 IU, Vitamin C is 1 mg-50,000 g, Vitamin E is 10 IU-40,000 IU, L-Arginine is 10 mg-100 g, Alpha lipoic acid is 10 mg-2000 mg, Lutein is 1 mg-1000 mg, Lycopene is 0.1 g-1000 mg, Marigold flower extract is 1 g-15,000 mg, Saffron extract is 1 g-10,000 mg, Pine bark extract is 1 g-10,000 mg, Grape seed extract is 1 mg-10,000 mg, Bilberry extract is 1 mg-5000 mg and Zinc is 0.1 mg-1000 mg in the nutrient mixture.

* * * * *